United States Patent
Pliner et al.

(10) Patent No.: US 6,758,282 B2
(45) Date of Patent: Jul. 6, 2004

(54) FIRE PROTECTION PIPE AND METHODS OF MANUFACTURE

(75) Inventors: David S. Pliner, Huntingdon Valley, PA (US); Manzoor Chaudhry, Bensalem, PA (US); Stephen T. Norvilas, Doylestown, PA (US); Elmer H. Foster, Mount Laurel, NJ (US); Robert D. Bussiere, Frankfort, IL (US)

(73) Assignee: Allied Tube & Conduit Company, Harvey, IL (US)

(*) Notice: Subject to any disclaimer, the term of this patent is extended or adjusted under 35 U.S.C. 154(b) by 322 days.

(21) Appl. No.: 09/955,426

(22) Filed: Sep. 18, 2001

(65) Prior Publication Data

US 2002/0060080 A1 May 23, 2002

Related U.S. Application Data

(60) Provisional application No. 60/233,676, filed on Sep. 19, 2000.

(51) Int. Cl.[7] .................................................. A62C 2/00
(52) U.S. Cl. .................................. 169/43; 169/5; 169/16; 138/145; 252/387; 252/390; 118/306; 118/318; 427/230; 427/236
(58) Field of Search .............................. 169/5, 13, 16, 169/43, 45, 46; 138/143, 145, 148, DIG. 6; 29/458; 252/387, 388, 390, 391, 392; 118/306, 317, 318, DIG. 10; 427/230, 233, 236

(56) References Cited

U.S. PATENT DOCUMENTS

| | | | |
|---|---|---|---|
| 3,088,796 A | * | 5/1963 | Kahler et al. ............... 252/391 |
| 3,342,895 A | | 9/1967 | Schmitz-Josten et al. |
| 3,453,124 A | | 7/1969 | Wurstner |
| 3,768,145 A | | 10/1973 | Ostrowski |
| 3,860,430 A | | 1/1975 | Walker et al. |
| 4,018,702 A | * | 4/1977 | Boffardi et al. ............. 252/390 |
| 4,197,091 A | * | 4/1980 | Gainer ...................... 252/390 |
| 5,718,027 A | | 2/1998 | Laumann |
| 5,803,180 A | | 9/1998 | Talley |
| 6,042,750 A | * | 3/2000 | Burlew ....................... 252/387 |
| 6,221,263 B1 | * | 4/2001 | Pope et al. ................... 169/13 |

OTHER PUBLICATIONS

PCT International Search Report mailed Feb. 13, 2002 (7 pages).
Tariq K. Bsharat, "Detection, Treatment, and Prevention of Microbiologically Influenced Corrosion in Water–Based Fire protection Systems," pp. 1–16 (Jun. 1998) National Fire Sprinkler Association, Inc., Patterson, New York, U.S.A.

* cited by examiner

Primary Examiner—Steven J. Ganey
(74) Attorney, Agent, or Firm—Banner & Witcoff, Ltd.

(57) ABSTRACT

A fire protection water sprinkler system, comprising at least one metal tube to carry water within the system, the metal tube having a coating on its interior surface comprising a quaternary ammonium salt in combination with a filming amine(s) and/or a synthetic oil.

17 Claims, 1 Drawing Sheet

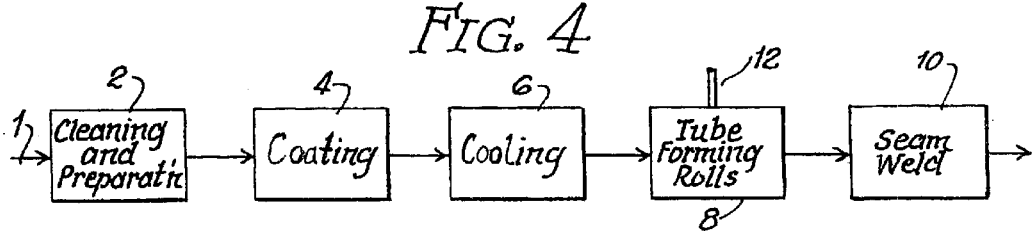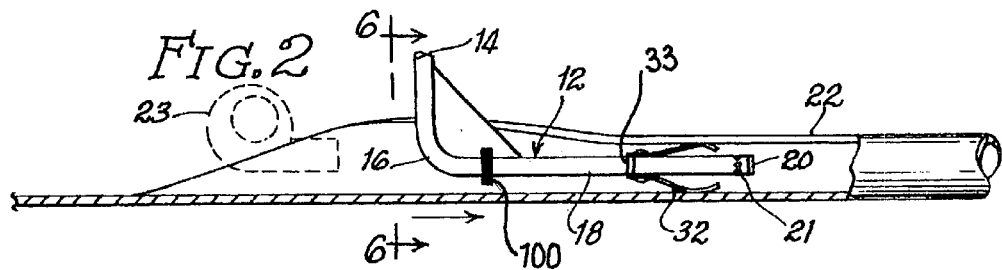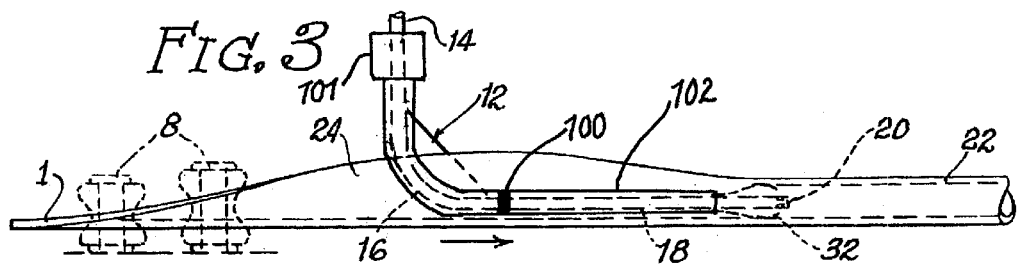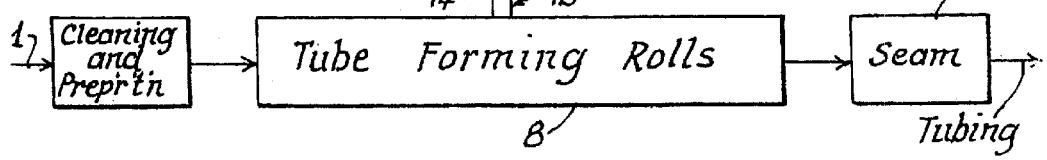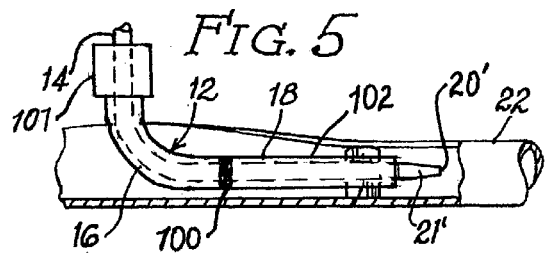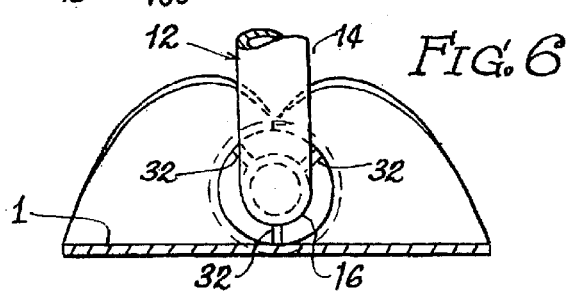

FIRE PROTECTION PIPE AND METHODS OF MANUFACTURE

CROSS-REFERENCE TO RELATED APPLICATIONS

This application is based on, and claims the benefit of, co-pending U.S. Provisional Application Serial No. 60/233,676, filed on Sep. 19, 2000, and entitled "Fire Protection Pipe And Methods of Manufacture."

FIELD OF THE INVENTION

The present invention relates to fire protection pipe and methods of manufacture thereof.

BACKGROUND OF THE INVENTION

This invention relates to inline coating of a metal substrate, such as a metal tube or conduit, of the type used for applications such as fire sprinkler systems for buildings. There are two types of fire sprinkler systems, wet and dry. When each type of system is first installed, the system is filled with air, then checked for leaks, then filled with water and again checked for leaks. The difference between the two systems is that for the dry system, the system is filled with water at a prescribed pressure for about 24 hours to check for leaks, and then drained, and the system is then pressurized with air, and then placed into operation. In the wet system, after the system is filled with water and it is confirmed that there are no leaks, the system is placed into operation without draining the water.

One of the major problems in both wet and dry sprinkler systems is the formation of microbiologically influenced corrosion ("MIC") on the interior surface of metal tubing. MIC arises from a wide variety of microbiological organisms called microbes including, but not limited to, sulfate reducing bacteria (SRB), acid forming bacteria (AFB), and slime formers. MIC can result in mechanical blockages of the piping and sprinkler heads, as well as premature perforation of steel tubing. MIC is a major cause of tuberculation, pitting and subsequent pipe failure in fire sprinkler systems. More specifically, MIC can cause tuberculation and corrosion, which can further lead to pinhole leaks in carbon steel, copper and galvanized pipe systems. It is not uncommon for a dry sprinkler system to have more severe MIC than a wet system, as there may be pockets of water in a dry system, as well as the presence of air, that lead to more severe MIC than with water alone.

Besides the problem of pinhole leaks that MIC creates, tubercles and nodules located on the interior of the pipe arising from MIC are a major concern as well since the pipe roughness factor (C-factor) that is applied to sprinkler piping used to determine friction loss does not anticipate severe MIC. See, e.g., "Detection, Treatment, and Prevention of Microbiologically Influenced Corrosion in Water-Based Fire Protection Systems," by Tariq K. Bsharat, Technical Services Manager of the NFSA, June 1998, which is incorporated herein by reference. In some cases of MIC, obstructions caused by tubercles are so great that there is almost no cross-sectional area of the opening in the pipe remaining. Id.

Fire sprinkler systems provide a favorable environment for the growth and development of bacteria resulting in MIC failures, as recognized by members of the American Fire Sprinkler Association ("AFSA"), National Fire Protection Association ("NFPA"), National Fire Sprinkler Association, Inc. ("NFSA"), National Association of Corrosion Engineers ("NACE"), sprinkler manufacturers, end users, and the fire protection service/mechanical contractors working within the industry. See, e.g., "Detection, Treatment, and Prevention of Microbiologically Influenced Corrosion in Water-Based Fire Protection Systems," by Tariq K. Bsharat, Technical Services Manager of the NFSA, June 1998.

Bacteria are either aerobic (i.e., thrive when exposed to oxygen) or anaerobic (inhibited or perish when exposed to oxygen). Aerobic microorganisms and their secretions on wetted pipe surfaces leads to the formation of biofilms, which frequently become embedded with iron, scale, oil, dirt, and other debris. This biofilm adheres to these metal surfaces and forms a gel-like mass around bacterial deposits, which promotes the formation of differential oxygen cell corrosion. As previously noted, MIC can result in mechanical blockages of the piping and sprinkler heads, as well as premature perforation of steel tubing.

Anaerobic bacteria, such as the class *Desulfovibrio desulfuricans* (sulfate reducers) and acid producers, seek out and colonize beneath the spotty biofilms (slime layers), under debris or inside porous tubercles where the environment is deficient or devoid of oxygen. These bacteria produce metal sulfides as corrosion products and, when exposed to air or hydrochloric acid, the rotten egg odor of hydrogen sulfide ($H_2S$) is easily detected. Sulfate reducing bacteria (SRB) are typical examples of anaerobic MIC and can cause rapid pitting and severe metal loss, accompanied by the $H_2S$ odor and black colored water frequently found in fire sprinkler systems. Another type of anaerobic bacteria is acid producing bacteria ("APB", which is sometimes referred to as acid forming bacteria ("AFB")). APB can be found in aerated microenvironments. One type of APB is called Clostridium, which can produce organic acids and stimulate SRB growth. Clostridium is a very important MIC microbe in carbon steel systems.

Aerobic sulfur oxidizing bacteria of the type thiobacillus can create an environment of up to about 10% sulfuric acid, thereby creating rapid corrosion. A layer of aerobic bacteria can also create a prime location in the system for anaerobic bacteria to thrive, since little or no oxygen is available below such a layer.

Prior attempts to reduce or eliminate the corrosion problems due to MIC have numerous drawbacks. A major drawback in prior techniques to treat MIC is that most of them involve treatment after MIC has already occurred and/or treatment that is post manufacture and installation of the sprinkler system.

Other drawbacks of prior attempts to treat MIC are expensive and time consuming. For example, prior attempts to treat MIC include replacement of pipe, which is extremely costly and is a time consuming operation.

Another approach is to flush the system with water. However, this can result in layers upon layers of aerobic and anaerobic bacteria as well as introduce new microbes and oxygen nutrients to the system, thereby allowing new MIC colonies to form.

Yet another approach is to drain the water out of the system, and then circulate an acidic solution throughout the entire piping system to dissolves tubercles and nodules formed by the MIC. This option requires that each sprinkler be removed and connected to hoses which connect to the main drain and to a special external pump. The acidic solution is circulated from 24 to 48 hours throughout every line and sprinkler to ensure that all corrosion deposits are dissolved. The cost of this type of treatment is about 25% to 50% of replacement of the entire piping system. See, e.g., "Detection, Treatment, and Prevention of Microbiologically Influenced Corrosion in Water-Based Fire Protection Systems," by Tariq K. Bsharat, Technical Services Manager of the NFSA, June 1998.

Another treatment for MIC is to raise the level of pH of the water in the system to a level in which microbes cannot grow. See, e.g., U.S. Pat. No. 5,803,180, which discloses a structure and method for adjusting the pH level to a value of between 9.5 and 11. However, this method is not recommended since it does not provide a solution for the removal of existing debris. See, e.g., "Detection, Treatment, and Prevention of Microbiologically Influenced Corrosion in Water-Based Fire Protection Systems," by Tariq K. Bsharat, Technical Services Manager of the NFSA, June 1998. Remaining nodules and tubercles can affect the flow of water and thereby add to friction loss in sprinkler pipe and tube. Id.

Another approach is to try a physical treatment called "pigging," in which a cylindrical apparatus is fitted in specific pipe sizes. The apparatus is placed on one end of the system and large pressure is applied sending the apparatus down a run of pipe, de-scaling the walls and removing the MIC tubercles. The problem with this treatment is that it only works for one pipe size at a time. For example, a 2-inch pig only works for 2-inch pipes. Therefore, this treatment is expensive and tedious, especially since the path of travel for the pig must be isolated from cross-mains and branch lines to conserve pressure. See, e.g., "Detection, Treatment, and Prevention of Microbiologically Influenced Corrosion in Water-Based Fire Protection Systems," by Tariq K. Bsharat, Technical Services Manager of the NFSA, June 1998.

Another approach is to flush the system with water that contains a biocide. However, this approach typically requires consultation with a MIC specialist for the type and amount of biocide to use to treat the MIC problem. See, e.g., "Detection, Treatment, and Prevention of Microbiologically Influenced Corrosion in Water-Based Fire Protection Systems," by Tariq K. Bsharat, Technical Services Manager of the NFSA, June 1998. Further, this treatment approach typically requires a flushing of the biocide through the system for a period of time, and then introducing the same biocide to treat the water that will be introduced into the system. Id. A drawback of this approach is that it requires continuous treatment with a biocide. Further, this approach requires choosing the correct biocide and amount, taking into account the chemical composition of the water, e.g., pH level, temperature, and levels of ammonia, chlorine, iron, manganese, and hardness, all of which can fluctuate over time. Further, the biocides used in accordance with this approach may be potentially dangerous, and can result in fines by environmental authorities if discharged improperly. Id. Examples of biocides include chlorine, iodine, hydrogen peroxide and ozone. Id.

It has also been recommended to place the piping system in as clean a condition prior to installation. For example, it has been recommended to avoid or remove dirt, excess cutting oils and standing water prior to installation of piping systems. See, "Detection, Treatment, and Prevention of Microbiologically Influenced Corrosion in Water-Based Fire Protection Systems," by Tariq K. Bsharat, Technical Services Manager of the NFSA, June 1998. However, this approach is difficult to put into actual practice given the work environment in the manufacture and installation of sprinkler systems.

SUMMARY OF THE INVENTION

Despite advances in the art, opportunity has remained for invention to avoid and/or eliminate MIC. In accordance with the present invention, the interior of sprinkler tubing is treated with an antibacterial solution prior to installation. The techniques of the present invention result in fire sprinkler tubing having resistance to MIC, thereby delaying and/or preventing the onset of MIC at the time the sprinkler tubing is first installed and thereafter. In a preferred embodiment, the antibacterial solution comprises a safe non-regulated, non-registered biostat comprising a quaternary ammonium salt in combination with a filming amine(s) and/or a synthetic oil. In a preferred embodiment, the antibacterial solution is applied to the interior surface of a sprinkler pipe or tube during manufacture of the tube, so as to form a mono-molecular film on the interior surface of the pipe. The applied coating results in a sprinkler tube that will minimize the formation of colonies of bacteria on the tube surface and also have some residual effect on other bacteria that may be introduced into the sprinkler system.

In accordance with the present invention, the antibacterial solution of the present invention can be applied via a continuous, controlled, in-line delivery system to spray the antibacterial solution on the interior of a sprinkler tube during the manufacturing process. Thus, the present invention provides a fire sprinkler tubing having a prophylactic film never previously taught or suggested by the prior art. Unlike the prior art, the present invention avoids and/or reduces the need for treatment for MIC after installation of the sprinkler system, and avoids the need for hazardous or toxic treatment materials that cannot be used in potable water systems.

As noted above, the prophylactic film of the present invention is preferably applied during the manufacturing process of the tube. Further, the film is non-toxic, in-line, and low cost. Moreover, the treated tubing is protected against MIC during storage, shipment, installation and testing of the sprinkler system prior to being placed into surface. Thus, the present invention eliminates and/or reduces contamination of the system prior to installation.

The manufacture of sprinkler tubing in accordance with the present invention includes the application of the biostat solution using any suitable technique. For example, see U.S. Pat. No. 3,768,145, which is incorporated herein by reference, which discloses various methods of in-line coating of the inside surface of galvanized tubing with paint or other protective films. See also U.S. Pat. No. 5,718,027, which is incorporated herein by reference, which discloses techniques for continuous formation of tubing, including the application of coatings to the interior of the tubing.

BRIEF DESCRIPTION OF THE DRAWINGS

FIG. 1 is a diagrammatic illustration of an apparatus embodying the invention;

FIG. 2 is a side view in cross section of a portion of the apparatus illustrated diagrammatically in FIG. 1;

FIG. 3 is a side view illustrating the apparatus of FIG. 1;

FIG. 4 is a diagrammatic illustration of an alternative apparatus embodying the invention;

FIG. 5 is a side view in cross section of a portion of the apparatus of FIG. 4;

FIG. 6 is an end view along the lines 6—6 of FIG. 2;

FIG. 7 is a cross-sectional view of coated tubing produced in accordance with the invention;

FIG. 8 is an illustration of a first embodiment of a lance usable in accordance with the invention; and FIG. 9 is an illustration of another embodiment of a lance usable in accordance with the invention.

DETAILED DESCRIPTION OF THE PREFERRED EMBODIMENTS

In accordance with the present invention, the interior of a metal substrate, such as sprinkler tubing, is treated with an antibacterial solution prior to installation. Although the invention is applicable to various metal substrates that may be susceptible to MIC, including fire sprinkler systems, it will be described by way of example principally in connection with tubing in fire sprinkler systems. The techniques of the present invention result in fire sprinkler tubing having resistance to MIC, thereby delaying and/or preventing the onset of MIC when the sprinkler tubing is first installed. In a preferred embodiment, the antibacterial solution comprises a safe non-regulated, non-registered biostat comprising a combination of a quaternary ammonium salt and filming amines.

In another preferred embodiment, the antibacterial solution comprises a safe non-regulated biostat comprising a combination of a quaternary ammonium salt and a synthetic oil. Antibacterial solutions having a quaternary ammonium salt in combination with a filming amine(s) or a synthetic oil are commercially available from multiple sources.

In a preferred embodiment, the antibacterial solution is applied to the interior surface of a sprinkler pipe or tube during manufacture of the tube, so as to form a monomolecular film on the interior surface of the pipe. The applied coating results in a sprinkler tube that will minimize the formation of colonies of bacteria on the tube surface, and also have some residual effect on other bacteria that may be introduced into the sprinkler system. In accordance with the present invention, the antibacterial solution of the present invention can be applied via a continuous, controlled, in-line delivery system to spray the antibacterial solution on the interior of a sprinkler tube during the manufacturing process. Preferably, the coating is applied to the interior diameter of the pipe after the pipe has been formed and seam welded.

Thus, the present invention provides a fire sprinkler tubing having a prophylactic film never previously taught or suggested by the prior art. Unlike the prior art, the present invention avoids and/or reduces the need for treatment for MIC after installation of the sprinkler system, and avoids the need for hazardous or toxic treatment materials that cannot be used in potable water systems. As noted above, the prophylactic film of the present invention is applied during the manufacturing process of the tube. Further, the film is non-toxic, in-line, and low cost. Moreover, the treated tubing is protected against MIC during storage, shipment, installation and testing of the sprinkler system prior to being placed into surface. Thus, the present invention eliminates and/or reduces contamination of the system prior to installation.

The manufacture of sprinkler tubing in accordance with the present invention includes the application of the biocide solution using any suitable technique. For example, see U.S. Pat. No. 3,768,145, which is incorporated herein by reference, which discloses various methods of in-line coating of the inside surface of galvanized tubing with paint or other protective films. See also, U.S. Pat. No. 5,718,027, which is incorporated herein by reference, which discloses techniques for continuous formation of tubing, including the application of coatings to the interior of the tubing.

In the present invention, the apparatus disclosed in U.S. Pat. No. 3,768,145 (incorporated by reference) may be used to apply the coating in accordance with the present invention. In FIG. 1, there is shown apparatus which includes means for preparing the surface of the flat strip steel for coating as it is fed from a source of such material. This constitutes a cleaning and preparation state 1 which may be an alkaline cleaner for cleaning the surface which is then rinsed from that surface. The surface is then treated with a suitable metal treatment such as a phosphate which is rinsed with water and then with chromic acid. Alternatively, if desired, the surface may be just prepared by washing it with a suitable ablative cleaner to assure a clean surface. If this is done, the cleaner must be rinsed in order to remove it completely.

In the embodiment of FIG. 1, a lance or elongated tube 12 is used. The lance 12 has a vertically extending portion 14 which is provided with means for connection to a source of paint (not shown). The portion 14 extends vertically downward through the tube forming rolls 8 intermediate their ends prior to the point where the rolls have brought the lateral edges of the flat strip together to form the complete tubing 22. The portion 14 is bent at 16 and extension 18 is provided to extend substantially parallel to the longitudinal axis of the tubing into the formed tubing past the point where the seam is to be welded. The extension 18 is provided at its free end with a nozzle 20. The nozzle 20 is designed to provide a spray of coating to completely cover the inside surface of the formed tubing 22. In the embodiment illustrated this may take the form of a nozzle or a series of nozzles having a plurality of holes 21 completely around its periphery to provide a spray of coating for 360°. In order to support the extension 18 and prevent it from rubbing against the surface of the tubing, suitable spacers such as a plurality of spring wires 32 may be provided to maintain the extension 18 in a relatively fixed position. The free ends of the wire, which are biased outwardly, bear against the interior wall of the tubing to support and center the extension 18.

Preferably, the apparatus of U.S. Pat. No. 3,768,145, as shown in FIGS. 1–9 herein, is modified so that lance 12 is long enough so that nozzle 20 sprays the coating onto the interior wall of the tubing at a point far enough from the weld area to avoid the coating on being exposed to high heat from welding. Preferably lance 12 is about 22–27 feet in length. In addition, in a preferred embodiment, lance 12 goes through an impeder 100 (not shown or disclosed in U.S. Pat. No. 3,768,145). Preferably, the impeder 100 surrounds the lance 12, and is about 3 feet downstream from the bend at 16. Preferably, the impeder 100 is about 1" to 2" in diameter. Those skilled in the art will recognize that the impeder 100 prevents heat flow to the lance from welding, and facilitates actual welding. In addition, the centering device preferably comprises removable and adjustable spring wires 32 that are not welded to the lance. More specifically, spring wires 32 are attached to lance 12 by a removable fastener 33.

Preferably, the application of the coating is done in an inert atmosphere. In order to produce a finished product in which the interior wall is smooth, that is, free of rough spots which may be caused by splatter accumulating on the interior wall from the welding operation, an inert purge gas such as nitrogen should be blown through the tube. This may be accomplished by providing a blower 23 or compressed gas source positioned where the tube forming is substantially complete and having an outlet into the formed tubing downstream of the welder. While air may be used as a purge gas, nitrogen or some other inert gas is preferred.

Preferably, as shown in FIG. 3, a nitrogen purge with brass tubing is used to provide an inert atmosphere. A paint manifold 101 provides nitrogen to the purge tube 102, and also provides connection of the coating supply line to lance 12.

In the alternative embodiment of FIG. 4, a coating stage 4 which may take the form of any one of several conventional devices for applying the antimicrobial solution coating is used after the cleaning and preparation stage 2. Regardless of what technique is used, it is important that only the flat surface be coated and that the lateral edges of the strip remain free of coating. Were coating applied to the lateral edges its presence would interfere with the welding of those edges at a subsequent point in the machine.

After coating the strip may then pass to a cooling stage 6 in which there may be provided any suitable source of cooling to set the applied coating.

After cooling, the coated strip then enters a series of tube forming rolls 8 which progressively bend the strip into a tubular configuration. After leaving the tube forming rolls, the formed tubing then passes to a welding stage 10. Welding may be achieved by any number of methods such as electrical resistance, RF welding, DC welding, etc. It may be desired to apply an additional amount of coating at the interior of the completed tubing 22 along the welded seam from which the coating has been burned off during welding to provide a completely coated interior surface.

FIGS. 8 and 9 illustrate alternative embodiments of suitable lance structures. In FIG. 8, the lance is constituted by a first tube 34 through which the coating material is conveyed. When cooling is required, secured to the first tube 34 is a second tube 36. The tube 36 is bent back upon itself at the outer end of the lance so that it provides two runs along the substantial length of the lance. The end of one run may be connected to a source of cooling water while the end of the other run is connected to a return to that source so that water may be caused to circulate through the tube 36 to maintain the temperature of the coating at a value where it will not commence to be cooled and gel in the lance. FIG. 9 comprises three concentric tubes wherein the coating is passed through the inner tube 38 and a center or intermediate tube 40 is connected to a source of cooling water.

The extension 18 is disposed substantially parallel to the longitudinal axis of the steel strip and the formed tubing and is of such a length as to extend into the tubing past the point where the lateral edges are brought completely together by the forming rolls to provide the seam to be subsequently welded. The length is also such that it extends into the formed tubing past the welding stage 10 and is provided at its free end with a nozzle 20' having an opening 21' aimed upwardly toward the welded seam from which coating has been burned off as a result of the welding operation. Coating supplied via the extension 14 is sprayed on that seam and on the adjacent surface of the interior wall of the tubing from which the coating has been burned to apply what might be characterized as a touch up coat in order that the interior surface will be completely coated as shown by reference numeral 19 in FIG. 7. It has been found that an airless coating spray system is particularly suitable for supplying coating through the lance. However, under certain circumstances conventional air spray systems can be used.

Table 1 depicts various nozzle numbers and identification thereof, and flow rates of coating at a given fluid pressure through the nozzle to achieve a tubing with a prophylactic film in accordance with the present invention. The nozzles are from Spraying Systems Company of Chadds Ford, Pa. 19397. The "SS" designation stands for stainless steel and the "TC" designation stands for tungsten carbide.

TABLE 1

| | | Flow Rate in Gallons Per Minute at Given psi | | |
|---|---|---|---|---|
| Nozzle Number and Identification | | 100 psi | 700 psi | 300 psi |
| 1. | 209860-1-SSTC 13052-012-TC Orifice 13324-05-SS-TC Core | 0.042 | 0.035 | 0.023 |
| 2. | 20986-2-SSTC 13052-016-TC Orifice 13324-05-SS-TC Core | 0.075 | 0.63 | 0.041 |
| 3. | 20986-3-SSTC 13052-022-TC Orifice 13324-06-SS-TC Core | 0.138 | 0.115 | 0.076 |
| 4. | 20986-4-SSTC 13052-029-TC Orifice 13324-07-SS-TC Core | 0.200 | 0.167 | 0.109 |
| 5. | 20986-5-SSTC 13052-037-TC Orifice 13324-07-SS-TC Core | 0.250 | 0.209 | 0.137 |
| 6. | 20986-6-SSTC 13052-037-TC Orifice 13324-08-SS-TC Core | 0.300 | 0.251 | 0.164 |
| 7. | 20986-7-SSTC 13052-041-TC Orifice 13324-08-SS-TC Core | 0.325 | 0.272 | 0.178 |
| 8. | 20987-8-SSTC 13052-046-TC Orifice 13324-08-SS-TC Core | 0.363 | 0.304 | 0.199 |
| 9. | 20987-9-SSTC 13052-055-TC Orifice 13324-08-SS-TC Core | 0.414 | 0.346 | 0.227 |
| 10. | 20987-10-SSTC 13052-064-TC Orifice 13324-08-SSTC Core | 0.494 | 0.413 | 0.271 |

Table 2 depicts the recommended nozzle for application of the coating as the tubing moves past the in-line coating apparatus for a given mill-speed-feet/minute rate. The nozzle numbers listed in Table 2 are identified in Table 1.

TABLE 2

RECOMMENDED NOZZLE FOR APPLICATION OF THE COATING AS THE TUBING MOVES PAST THE IN-LINE COATING APPARATUS FOR A GIVEN MILL-SPEED-FEET/MINUTE RATE PRODUCT

| Fence/ABF | 100 | 150 | 200 | 250 | 300 | 350 | 400 | 450 | 500 | 550+ |
|---|---|---|---|---|---|---|---|---|---|---|
| 1.315 | 2/3 | 2/3 | 4 | 4 | 4 | 4 | 4 | 5 | 5 | 5 |
| 1.660 | 4 | 4 | 4 | 4 | 4 | 5 | 5 | 5 | 5 | 5 |
| 1.900 | 2/3 | 2/3 | 3 | 4 | 4 | 5 | 5 | 5 | | |
| 1.375 | | 4 | 4/5 | 5 | 5 | 7 | 7 | | | |
| 2.875 | | 5 | 5 | 7 | 7 | | | | | |

TABLE 2-continued

RECOMMENDED NOZZLE FOR APPLICATION OF THE COATING
AS THE TUBING MOVES PAST THE IN-LINE COATING APPARATUS
FOR A GIVEN MILL-SPEED-FEET/MINUTE RATE PRODUCT

| EMT   | 200 | 250 | 300 | 350 | 400 | 450 | 500 | 550 | 600 | 650+ |
|-------|-----|-----|-----|-----|-----|-----|-----|-----|-----|------|
| 0.706 |     |     |     |     |     | 2   | 2   | 3   | 4   | 4    |
| 0.922 |     |     |     |     |     |     | 2   | 2   | 2   | 4    |
| 1.163 |     |     | 3   | 4   | 4   | 4   | 4   | 4   | 5   | 5    |
| 1.510 |     | 3   | 4   | 4   | 4   | 4   | 4   | 4   | 5   | 5    |
| 1.740 | 3   | 3   | 4   | 4   | 4   | 5   | 5   | 5   | 5   | 5    |
| 2.197 | 3   | 4   | 4/5 | 5   | 5   | 5   | 5   | 5   | 5   | 5    |

| IMC/ABF | 150 | 200 | 250 | 300 | 350 | 400 | 450 | 500 | 550 | 600+ |
|---------|-----|-----|-----|-----|-----|-----|-----|-----|-----|------|
| 0.815   |     |     |     |     |     |     | 2   | 2   | 3   | 4    |
| 1.029   |     |     |     |     |     |     |     | 2   | 3   | 4    |
| 1.638   | 3   | 3   | 4   | 4   | 4/5 | 4/5 | 5   | 5   | 5   | 5    |
| 1.883   | 3   | 4   | 4   | 4/5 | 5   | 5   | 5   | 5   | 5   | 5    |
| 2.360   | 3   | 4   | 4/5 | 5   | 5   | 5/7 | 5/7 | 5/7 | 7   | 7    |

EXAMPLES

The following examples further illustrate the benefits of the present invention and are not intended to limit or otherwise restrict the invention.

Example 1

Screening Tests of 1SCF 1698-41–42 and 1SCF 2602-47–02

The first set of tests were done to determine whether the compounds had any effect on MIC-related microbes. This was done as follows:

Compounds 1SCF 1698-41–42 and 1SCT 2602-47–02 were tested in undiluted form (1,000,000 ppm) and on product diluted in deionized water to provide final concentrations of 500,000 ppm, 250,000 ppm, and 125,000 ppm of product. These solutions were prepared in sterile test tubes. A control containing only deionized water was included.

One-tenth milliliter (ml) of a solution containing approximately 10,000,000 bacteria per ml of two each of the following microbes was then added to each test tube: sulfate reducing bacteria, acid producing bacteria (including spore forming APB), iron depositing bacteria and low nutrient bacteria (including slime forming aerobic bacteria). The test microbes included standard strains and strains growth from actual "real-world" cases of MIC.

Aliquots of the test solutions were removed after 24 hours inoculated into growth media for the enumeration of MIC-related bacteria (MICkits). These were incubated for 15 days and the results recorded. The results of these tests are shown in Table 3 under the headings "First Test 1SCF 1698-41–42). Note that a result of >1,000 per ml is the maximum detection limit for the test as performed. The actual number of bacteria per ml was likely much higher.

These data demonstrated that 1SCF 1698-41–42, which was a quaternary ammonium salt in a synthetic oil, was effective in controlling the growth of microbes. In fact, all bacteria in the test solutions were killed.

These data also demonstrate that 1SCF 2602-47–02, which was tap water, was not effective in controlling the growth of MIC microbes.

TABLE 3

TEST OF INHIBITORS AGAINST MIC BACTERIA
(INCLUDING LNB, IRB, APB, AND SRB) SCREENING TESTS

| | Viable Bacteria Test Results | | |
|---|---|---|---|
| | LNB | APB | SRB |
| FIRST TEST 1SCF 1698-41-42 | | | |
| Test Solution | | | |
| 10 ml INHIB + 0.1 ml MIC Bacteria | No Growth | No Growth | |
| 5 ml INHIB + 5 ml distilled H$_2$O + 0.1 ml MIC Bacteria | No Growth | No Growth | |
| 3.3 ml INHIB + 0.1 ml MIC Bacteria | No Growth | No Growth | |
| 1 ml INHIB + 0.1 ml MIC Bacteria | No Growth | No Growth | |
| Control | Growth | Growth | |
| FIRST TEST 1SCF 2602-47-02 | | | |
| Test Solution | | | |
| 10 ml INHIB + 0.1 ml MIC Bacteria | No Growth | No Growth | |
| 5 ml INHIB + 5 ml distilled H$_2$O + 0.1 ml MIC Bacteria | Growth | Growth | |
| 3.3 ml INHIB + 0.1 ml MIC Bacteria | Growth | Growth | |
| 1 ml INHIB + 0.1 ml MIC Bacteria | Growth | Growth | |
| Control | Growth | Growth | |
| SECOND TEST 1SCF 1698-41-42 | | | |
| Concentration Inhibitor (PPM of Product) | | | |
| 100,000 | No Growth | No Growth | No Growth |
| 10,000 | No Growth | No Growth | No Growth |
| 5,000 | No Growth | No Growth | No Growth |
| 2,500 | No Growth | No Growth | No Growth |
| 1,250 | Growth | Growth | No Growth |
| 625 | Growth | Growth | No Growth |
| 312 | Growth | Growth | No Growth |
| 156 | Growth | Growth | No Growth |

TABLE 3-continued

TEST OF INHIBITORS AGAINST MIC BACTERIA
(INCLUDING LNB, IRB, APB, AND SRB) SCREENING TESTS

| | Viable Bacteria Test Results | | |
|---|---|---|---|
| | LNB | APB | SRB |
| 78 | Growth | Growth | No Growth |
| Control | Growth | Growth | Growth |

Key to Abbreviations:
ml = Milliliter
INHIB = Inhibitor
LNB = Low Nutrient Bacteria
IRB = Iron-Related Bacteria
APB = Acid-Producing Bacteria
SRB = Sulfate-Reducing Bacteria Example 2

Second Screening Test of 1SCF 1698-41–42

A second set of tests for 1SCF 1698-41–42 was set up in the same manner as for the first set of screening tests, except that the concentrations of the inhibitor tested ranged from 100,000 ppm product down to 78 ppm product (see Table 3 under the heading "Second Test 1SCF 1698-41–42").

The results of the second screening test showed that the inhibitor controlled the growth of MIC-related bacteria (the same assemblage as used in the first screening test) at inhibitor concentrations of 2,500 ppm product or greater.

Example 3

Tests on First Set of Pipes

Tests were then conducted on three types of pipes—labeled A, B, and C. Each type of pipe was immersed in a plastic container containing two gallons of tap water and test suspension of MIC-related bacteria comparable to that used in the screening tests.

Each test was sampled after two and seven days by removing an aliquot of the test solution and processing into various MICkit media for the enumeration of MIC-related bacteria.

One of the four pieces of pipe from each test container was removed and gently rinsed with sterile deionized water to remove absorbed water.

One square inch of the interior surface of the test pipe was then swabbed using a sterile cotton swab. The swab was put into anaerobic diluting solution to make a slurry of the surface associated materials taken from the pipe surface. This slurry was then processed into MICkit media as for the liquid samples.

All MICkit growth media were read after fifteen days incubation and the results recorded.

The results are shown in Table 4 under the heading "First Pipe Tests."

The results demonstrated that both pipe B (coated with a quaternary ammonium salt and filming amines) and pipe C (coated with a quaternary ammonium salt and a synthetic oil) killed all types of bacteria in the water and prevented viable bacteria from growing on the internal pipe surface.

TABLE 4

TEST OF PIPES AGAINST MIC BACTERIA
(INCLUDING LNB, APR, AND SRB)

| | Viable Bacteria Test Results | | |
|---|---|---|---|
| | LNB | APB | SRB |
| FIRST PIPE TESTS | | | |
| Sample Time Elapsed | | | |
| PIPE A-WATER/2 DAYS | >1,000 | >1,000 | >1,000 |
| PIPE A-PIPE SURFACE/7 DAYS | >1,000 | >1,000 | >1,000 |
| PIPE A-WATER/7 DAYS | >1,000 | >1,000 | >1,000 |
| PIPE A-PIPE SURFACE/7 DAYS | >1,000 | >1,000 | >1,000 |
| PIPE B-WATER/2 DAYS | 0 | 0 | 0 |
| PIPE B-PIPE SURFACE/7 DAYS | 0 | 0 | 0 |
| PIPE B-WATER/7 DAYS | 0 | 0 | 0 |
| PIPE B-PIPE SURFACE/7 DAYS | 0 | 0 | 0 |
| PIPE C-WATER 2 DAYS | 0 | 0 | 0 |
| PIPE C-PIPE SURFACE 7 DAYS | 0 | 0 | 0 |
| PIPE C-WATER 7 DAYS | 0 | 0 | 0 |
| PIPE C-PIPE SURFACE 7 DAYS | 0 | 0 | 0 |
| SECOND PIPE TESTS | | | |
| Sample | | | |
| PIPE A-WATER | >1,000 | >1,000 | >1,000 |
| PIPE A-PIPE SURFACE | >1,000 | >1,000 | >1,000 |
| PIPE B-WATER | >1,000 | >1,000 | >1,000 |
| PIPE B-PIPE SURFACE | >1,000 | >1,000 | >1,000 |
| PIPE C-WATER | >1,000 | >1,000 | >1,000 |
| PIPE C-PIPE SURFACE | >1,000 | >1,000 | >1,000 |
| PIPE F-WATER | >1,000 | >1,000 | >1,000 |
| PIPE F-PIPE SURFACE | >1,000 | >1,000 | >1,000 |
| PIPE S-WATER | >1,000 | >1,000 | >1,000 |
| PIPE S-PIPE SURFACE | >1,000 | >1,000 | >1,000 |
| PIPE W-WATER | >1,000 | >1,000 | >1,000 |
| PIPE W-PIPE SURFACE | >1,000 | >1,000 | >1,000 |

Key to Abbreviations:
LNB = Low Nutrient Bacteria
APB = Acid-Producing Bacteria
SRB = Sulfate-Reducing Bacteria Example 4

Tests on Second Set of Pipes

These tests were done as for the first set of pipe tests, except that the second batch of pipes were labeled with designations A, B, C, F, S and W.

The results of these tests are shown in Table 4 under the heading "Second Pipe Tests."

The results demonstrated that none of the pipes tested inhibited MIC-related bacteria either in test waters or on pipe surfaces. None of this set of test pipes was coated with a quaternary ammonium salt in combination with a filming amine or a synthetic oil.

Many modifications and variations may be made in the techniques and structures described and illustrated herein without departing from the spirit and scope of the present invention. Accordingly, the techniques and structures described and illustrated herein should be understood to be illustrative only and not limiting upon the scope of the present invention.

What is claimed is:

1. A fire protection water sprinkler system, comprising at least one metal tube to carry water within the system, the metal tube having a coating on its interior surface comprising a quaternary ammonium salt and a filming amine.

2. A fire protection water sprinkler system in accordance with claim 1, wherein the coating is effective for controlling the growth of microbiologically influenced corrosion on the interior surface of the metal tube.

3. A fire protection water sprinkler system in accordance with claim 2, wherein the coating is applied prior to installation of the system as a mono-molecular film on the interior surface of the metal tube.

4. A fire protection water sprinkler system in accordance with claim 1, wherein the coating further comprises a synthetic oil.

5. A method of manufacture of a fire protection water sprinkler system, comprising: (a) forming at least a metal tube, and (b) applying a coating on the interior surface of the metal tube, the coating comprising a quaternary ammonium salt and a filming amine, wherein step (b) is performed prior to installation of the fire protection water sprinkler system in a building.

6. A fire protection water sprinkler system made in accordance with claim 5.

7. A method of manufacture in accordance with claim 5, wherein the coating is applied on the interior surface of the metal tube in an amount effective for controlling the growth of microbiologically influenced corrosion on the interior surface.

8. A method of manufacture in accordance with claim 7, wherein the coating forms a mono-molecular film on the interior surface of the metal tube.

9. A method of manufacture in accordance with claim 7, wherein the growth of microbiologically influenced corrosion is inhibited subsequent to installation of the system without additional treatment.

10. A fire protection water sprinkler system, comprising at least one metal tube to carry water within the system, the metal tube having a coating on its interior surface comprising a quaternary ammonium salt and synthetic oil.

11. A fire protection water sprinkler system in accordance with claim 10, wherein the coating is effective for controlling the growth of microbiologically influenced corrosion on the interior surface of the metal tube.

12. A fire protection water sprinkler system in accordance with claim 11, wherein the coating is applied prior to installation of the system as a mono-molecular film on the interior surface of the metal tube.

13. A method of manufacture of a fire protection water sprinkler system, comprising: (a) forming at least a metal tube, and (b) applying a coating on the interior surface of the metal tube, the coating comprising a quaternary ammonium salt and a synthetic oil, wherein step (b) is performed prior to installation of the fire protection water sprinkler system in a building.

14. A fire protection water sprinkler system made in accordance with claim 13.

15. A method of manufacture in accordance with claim 13, wherein the coating is applied on the interior surface of the metal tube in an amount effective for controlling the growth of microbiologically influenced corrosion on the interior surface.

16. A method of manufacture in accordance with claim 15, wherein the coating forms a mono-molecular film on the interior surface of the metal tube.

17. A method of manufacture in accordance with claim 15, wherein the growth of microbiologically influenced corrosion is inhibited subsequent to installation of the system without additional treatment.

* * * * *